United States Patent [19]

Nagata et al.

[11] Patent Number: 4,821,573
[45] Date of Patent: Apr. 18, 1989

[54] ULTRASONIC METHOD OF INSPECTING CONTENTS OF A PACKAGE AND APPARATUS THEREOF

[75] Inventors: Masanori Nagata; Tsugio Kaneoka; Shigeki Imano; Hitoshi Matumoto, all of Tokyo, Japan

[73] Assignee: Fujimori Kogyo Co., Ltd., Tokyo, Japan

[21] Appl. No.: 106,846

[22] Filed: Oct. 13, 1987

[30] Foreign Application Priority Data

Oct. 15, 1986 [JP]   Japan ................................. 61-245115
Jan. 13, 1987 [JP]   Japan ................................... 62-5528
Jan. 28, 1987 [JP]   Japan .................................. 62-18035

[51] Int. Cl.⁴ .......................................... G01M 3/00
[52] U.S. Cl. ...................................... 73/597; 73/599; 73/52
[58] Field of Search ................. 73/596, 597, 598, 599, 73/600, 618, 52, 54, 865.8, 53, 61 R, 32 A; 209/520, 523, 524, 536, 552, 576, 577, 600, 601, 604, 590

[56] References Cited

U.S. PATENT DOCUMENTS

| | | | |
|---|---|---|---|
| 2,277,037 | 3/1942 | Clark et al. | 73/596 |
| 2,378,237 | 6/1945 | Morris | 73/600 |
| 3,074,267 | 1/1963 | Martin | 73/600 |
| 3,357,556 | 12/1967 | Martner et al. | 73/52 |
| 3,384,767 | 5/1968 | Arnold et al. | 73/600 |
| 3,553,636 | 1/1971 | Baird | 73/597 |
| 3,913,383 | 10/1975 | Kreula et al. | 73/52 |
| 3,918,293 | 11/1975 | Feigel | 73/52 |
| 4,023,400 | 5/1977 | November | 73/54 |
| 4,208,915 | 6/1980 | Edwards | 73/639 |
| 4,656,866 | 4/1987 | Aarts | 73/52 |
| 4,697,452 | 10/1987 | Prakken | 73/52 |

FOREIGN PATENT DOCUMENTS 57-15327  3/1982  Japan .
58-52179 11/1983  Japan .
58-53855 12/1983  Japan .

Primary Examiner—Stewart J. Levy
Assistant Examiner—Robert R. Raevis
Attorney, Agent, or Firm—Armstrong, Nikaido Marmelstein & Kubovcik

[57] ABSTRACT

The invention provides an ultrasonic method of inspecting contents (fluid food, for instance) of a package by disposing an ultrasonic transmitter-receiver system on at least one side of the package and evaluating the occurrence or degree of degradation of the contents on the basis of output data from the system. The invention also provides an ultrasonic apparatus for inspecting contents of a package which comprises a shaking device for feeding and shaking the package, an ultrasonic device disposed independently and downstream of the shaking device, and a guide device for feeding the package downstream of the shaking device to the ultrasonic device and further downstream.

6 Claims, 3 Drawing Sheets

ULTRASONIC METHOD OF INSPECTING CONTENTS OF A PACKAGE AND APPARATUS THEREOF

BACKGROUND OF THE INVENTION

This invention relates to an ultrasonic method for quality testing of packaged products.

The degradation of foods contained in bags and pouches can be easily ascertained, for example by the visual inspection of the packages for signs of expansion when the contents liberate gases on putrefaction or degradation and, hence, cause expansion of the containing bags or by the visual inspection of the contents through the bags, provided that the bags are of the see-through type, when the contents putrefy or degrade without evolution of gases. If the bags cannot be seen through, an appropriate number of samples are taken at random, the bags are broken and the contents are visually inspected.

However, the visual inspection for the expansion of bags is valid only when the putrefaction has progressed to a marked extent and cannot be a useful method at an early or intermediate stage of putrefaction where the evolution of gases is not large enough, for the lack of expansion of a bag does not necessarily mean that the contents have not undergone degradation or putrefaction.

The visual inspection through light-transparent bags is not successful, either, at a stage where spoilage has not progressed far enough. Thus, it is inevitable to destroy the bags for confirmation.

Recent foods are often available as packaged in aluminum foil-laminated plastic film and, in such cases, the above destructive inspection method is the only method available.

However, the method comprising sampling out a large number of packages and testing them is very disadvantageous in terms of procedural complexity. Moreover, since even acceptable products are made unacceptable by unpackaging, this method has the drawback of increased unit production cost. For a complete quality check, the sample size must be sufficiently large but since it is impossible to unpackage so many products, the method is inadequate in reliability.

Further, irrespective of whether the bags are transparent and the contents are visible from outside or the bags are made of opaque material and broken for inspection of the contents, the visual examination is not necessarily a reliable method of inspection. Moreover, the examination accuracy is dependent on individual inspectors.

It is, therefore, an object of this invention to provide a non-destructive method for accurate evaluation of packaged products for spoilage and other quality parameters.

It is another object of this invention to provide an apparatus which can be advantageously employed for the purpose of practicing the above-mentioned non-destructive method.

SUMMARY OF THE INVENTION

The ultrasonic method for evaluation of packaged products for spoilage or the like change in accordance with this invention is generally such that an ultrasonic transmitter-receiver system is disposed on at least one side of the package and the occurrence or degree of spoilage, degradation or other change in the contents is determined from output values from the ultrasonic transmitter-receiver system.

The apparatus used for practicing the above method according to this invention comprises an ultrasonic apparatus for inspecting contents of a package 1 which comprises a shaking device 2 for feeding and shaking the package 1, an ultrasonic device 3 disposed independently and downstream of the shaking device 2, and a guide device 4 for feeding the package 1 downstream of the shaking means 2 to the ultrasonic means 3 and further downstream. The shaking device 2 comprises a feed belt 21 for gripping the body of the package 1 and feeding the package 1 downstream and a shaking unit 22 for shaking the package 1 traveling with the feed belt 21. The ultrasonic device 3 comprising a water tank 31 for immersing the package 1, a body thickness limiter 32 for keeping a constant the thickness of the body of the package 1 in the water tank 31, and an ultrasonic transmitter-receiver system 33 to transmit an ultrasonic wave to the package 1 whose body thickness is kept constant by the body thickness limiter 32 and receive the transmitted or reflected wave. The guide device 4 comprises a gripping device 41 for gripping the package 1 and a guide device 42 for feeding the gripping device 41.

BRIEF DESCRIPTION OF THE DRAWINGS

FIGS. 4 and 5 each is a schematic view showing a body thickness limiter 32 which comprises a juxtaposed pair of rails 32a and 32a;

DETAILED DESCRIPTION OF THE INVENTION

Figure 1:
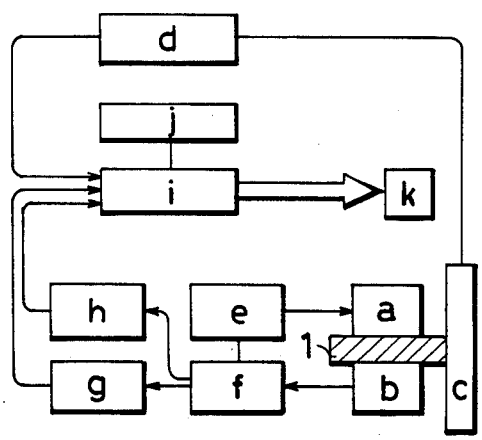
FIG. 1 is a block diagram showing an exemplary inspection method wherein the transmitted wave is used as a marker value.

This invention is hereinafter described in detail.

The wrapping material which constitutes a package may be any of single or multi-layer plastic packaging materials; composite sheet packaging materials made by lamination of a metal foil, metal-deposited plastic film or paper sheet with a plastic film or films; synthetic resin-clad natural or synthetic textile webs, and other flexible packaging materials and is preferably a packaging material carrying a heat-sealable layer as the innermost layer.

The form of package may be a bag, plastic bottle, bag-in-box, plastic tube, laminate tube, paper carton or the like.

When the packaging form is a bag, it may for example be triangular, gusset-shaped, or free-standing.

The contents of packages may be foods, pharmaceutical agents, feedstuffs and so on, although foods are of particular importance in the context of this invention. The contents may be of any desired consistency only if it is freely-flowable, such as a homogeneous solution, a dispersion, a paste, or the like.

Before it is subjected to the ultrasonic inspection to be described hereinafter, the package is preferably shaken so as to disperse the head space (plenum within the packaging material) into the contents. However, depending on the types of contents, this shaking process may be omitted.

In accordance with the present invention, an ultrasonic wave is directed to the package to be inspected from a ultrasonic transmitter-receiver system disposed on at least one side of the package.

The ultrasonic transmitter-receiver system may be disposed either in contact with the exterior surface of the package or at a short distance therefrom (provided that the distance should be kept constant). The system may also be disposed on the exterior wall surface of the water tank. In either case, the presence of water between the exterior surface of the package and the ultrasonic transmitter-receiver system contributes to a reduced error. It is, therefore, advisable to subject the package to the ultrasonic inspection while it is immersed in water.

The transmission and reception of ultrasonic waves can be effected in the following two alternative modes.

In one mode, the ultrasonic transmitter is disposed on one side of the package and the ultrasonic receiver on the other side so that the latter receives the ultrasonic wave transmitted through the package.

In the other mode, both the ultrasonic transmitter and receiver are disposed on one side of the package so that the receiver may receive the reflected ultrasonic wave. While the transmission of the ultrasonic wave and the reception of the reflected wave are generally carried out with the same ultrasonic transmitter-receiver, it is possible to install an ultrasonic transmitter and an ultrasonic receiver independently of the same side of the package.

By transmitting and receiving the ultrasonic wave in the above manner, there can be obtained varied outputs, e.g. (1) the difference in sonic velocity between a transmission wave and a reception wave or the sonic velocity of reception wave, (2) the time from transmission to reception, and (3) the degree of attenuation of ultrasonic energy. Therefore, in accordance with this invention, the occurrence and degree of degradation of the contents is evaluated based on at least one of such outputs. It should be understood that the reception wave is either the transmitted wave or the reflected wave.

The useful wavelength region of ultrasonic wave is about 0.5 MHz to about 20 MHz.

In performing the determination, only the wave of a single frequency can be employed but the accuracy of evaluation can be further improved by using a few selected frequencies for the transmission wave.

FIG. 1 is a block diagram showing an exemplary inspection method using the transmitted wave as a marker.

The reference numeral 1 indicates a package comprising a bag containing the contents to be inspected for degradation. a is an ultrasonic transmitter disposed on one side of the package 1, b is an ultrasonic receiver disposed on the other side of the package 1, c a magnet scale, d a length measurement converter, e a transmission circuit, f a reception circuit, g a propagation attenuation detection circuit, h a propagation time detection circuit, i an operation circuit, and j a display circuit. The data k is output in the direction of the open arrowmark.

Figure 2:
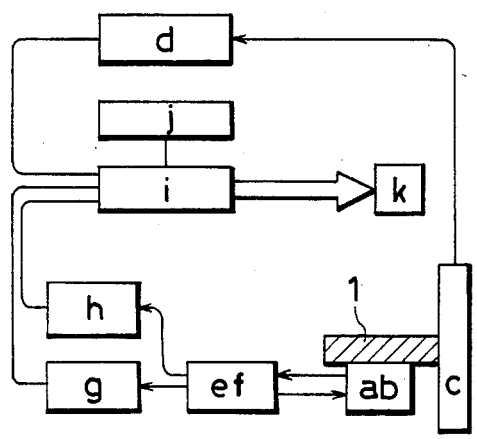
FIG. 2 is a block diagram showing an exemplary inspection method wherein the reflected wave is used as a marker value.

FIG. 2 is a block diagram showing an exemplary inspection method using the reflected wave as a marker.

The symbol ab represents an ultrasonic transmitter-receiver disposed on one side of the package 1; ef a transmission-reception circuit. The other symbols have the same meanings as those assigned to the like symbols in FIG. 1.

When the transmitted wave is to be used as a marker as in the mode of FIG. 1, it is so arranged that both the thickness of the package 1 and the distance between transmitter a and receiver b are kept constant and, in that condition, an ultrasonic wave of a given frequency is transmitted from the ultrasonic transmitter a while the transmitted wave through the package 1 is received by the receiver b.

When the reflected wave is used as a marker as in the mode of FIG. 2, it is so arranged that the thickness of the package is kept constant, and an ultrasonic wave of a given frequency is transmitted from a transmitter-receiver disposed on one side of the package while the reflected wave is returned as reflected by the other side of the package 1 or a reflector, disposed on the other side, is received by the same transmitter-receiver.

If the contents of the package undergoes degradation, there occurs a change in specific gravity or viscosity, with the result that differences are found from the fresh product in the scattering, diffusion and absorption of the ultrasonic wave and, hence, differences in various marker values such as the sonic velocity difference between transmission and reception waves or the sonic velocity of reception wave, the time interval from transmission to reception, the degree of attenuation of ultrasonic energy, and so on.

Particularly if the package is subjected to a shaking procedure prior to the ultrasonic inspection, the head space (plenum) is dispersed into the contents so that even a slight variation in specific gravity or viscosity results in a magnified difference in the scattering, diffusion or absorption and, hence, in a large difference in output value, thus contributing to an increased accuracy of estimation.

Moreover, if an optimum frequency and marker are pre-selected for each inspection purpose or type of package on a basis of trial advance use of several transmission frequencies, a higher accuracy of evaluation can be realized.

The inspection method according to this invention assures the following beneficial results.

(1) Packaged product can be inspected irrespective of whether or not spoilage results in the evolution of gases.
(2) Since the package is not destroyed, there is no loss due to inspection.
(b 3) Not only the occurrence of spoilage but also the degree of degradation can be ascertained.
(4) Satisfactory detection accuracy is assured irrespective of the construction of the package or the type of contents.
(5) Since the method is more accurate than visual inspection for some kinds of contents, degradation which might be overlooked in visual inspection can be successfully detected.
(6) Rapid determination is possible.
(7) The inspection reliability is high, for not only samples but all products can be inspected on line.
(8) The method is free of individual difference in evaluation.
(9) The equipment cost is minimal and since the required number of inspectors is small as compared with visual inspection, the method is laborsaving, too.

The apparatus for practicing the above method is described below in detail.

Figure 3:
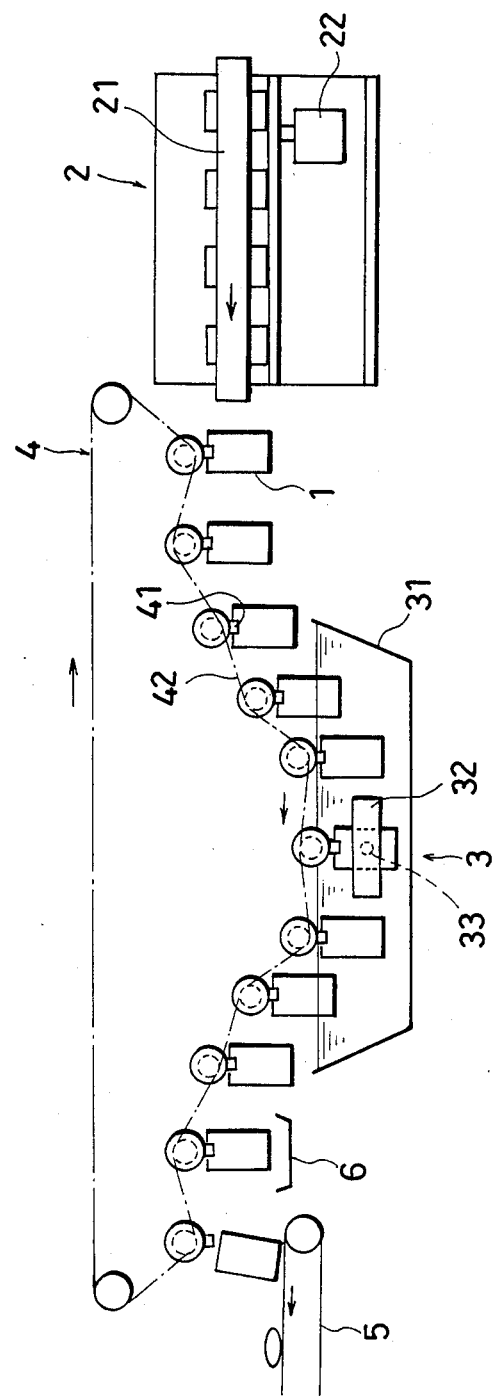
FIG. 3 is an overall view illustrating an exemplary inspection apparatus of this invention.

FIG. 3 is an overall view showing an exemplary inspection apparatus of this invention.

The inspection apparatus according to this invention comprises a shaking means 2 for feeding and shaking the package 1, an ultrasonic means 3 disposed downstream and independently of the shaking means 2, and a guide means 4 for feeding the package 1 emerging from the shaking means 2 to the ultrasonic means 3 and further downstream.

The shaking means 2 and ultrasonic means 3 are independently disposed to avoid the influence of the shaking motion of the former means 2 on the ultrasonic determination by the latter means 3, which could result in a large determination error by the ultrasonic transmitter-receiver system 33 which is described hereinafter.

The shaking means 2 comprises a feed belt 21 for gripping the body of the package 1 and feeding the package 1 downstream, a shaking unit 22 for shaking the package 1 traveling together with the feed belt 21, and accessory parts.

The feed belt 21 may feed the package 1 in an erected position or on its side. FIG. 3 shows the package fed in erected position.

The shaking unit 22 may be of an optional type, such as one wherein the rotary motion of a motor is transformed into a sinusoidal linear motion by means of a crankshaft and a rod, one utilizing the attractive force of an electromagnet, one using a vibrating motor (which utilizes the centrifugal force generated by revolution of a motor having imbalance weights on its shaft ends), one using a mechanical vibrator, or one using an ultrasonic vibrator.

The ultrasonic means 3 comprises a water tank or trough 31 for immersing the package 1, a body thickness limiter 32 for keeping a constant body thickness of the package 1 within the water tank 31, an ultrasonic transmitter-receiver system 33 for transmitting an ultrasonic wave to the package 1 whose body thickness is kept constant by the body thickness limiter 32 and receiving the transmitted wave or reflected wave, and accessory component parts.

The transmission of ultrasonic wave in an aqueous medium is effective in the sense that if there is air between the exterior surface of the package 1 and the ultrasonic transmitter-receiver system 33, the detection error of the system 33 will be large.

In conducting the ultrasonic inspection, it is necessary that the body thickness of the package 1 is kept constant. Therefore, a body thickness limiter 32 is provided so as to control the body thickness of the package 1 in water.

Figure 4:
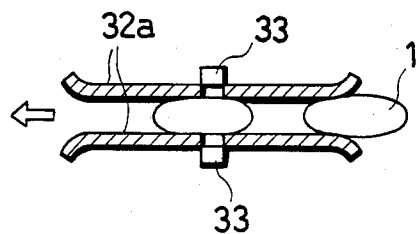
Figure 5:
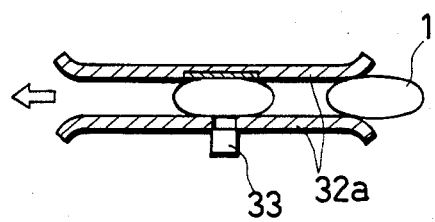

FIGS. 4 and 5 each is a schematic view showing the body thickness limiter 32 which comprises a juxtaposed pair of rails 32a and 32a. In appropriate positions of the rails 32a, 32a, there is provided an aperture, slot or cavity for application of an ultrasonic wave. While the material of the rails 32a, 32a is optional, it is preferably a light-transparent material such as a polymethyl methacrylate plate, a polycarbonate plate or the like.

In FIG. 4, the transmission unit of the ultrasonic transmitter-receiver system 33 is disposed in the aperture, slot or cavity of one of the rails 32a and the reception unit of the same system 3 is disposed in the aperture, slot or cavity of the other rail 32a. In this arrangement, the transmitted wave is determined.

In FIG. 5, the transmission and reception units of the ultrasonic transmitter-receiver system 33 are installed in the aperture, slot or cavity of one of the rails 32a, 32a, while a reflector plate is installed in the aperture, slot or cavity of the other rail 32a. In this arrangement, it is the reflected wave that is determined.

Figure 6:
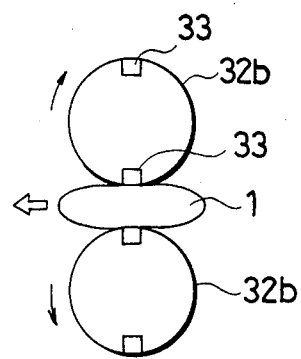
FIGS. 6 and 7 each is a schematic view showing a body thickness limiter 32 which comprises a juxtaposed pair of knurls 32b and 32b.
Figure 7:
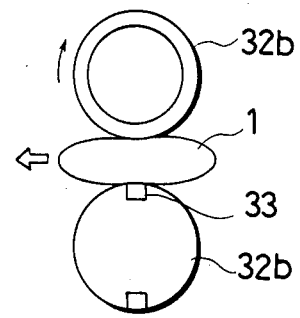

FIGS. 6 and 7 each shown a schematic view of the body thickness limiter 32 which is comprised of a juxtaposed pair of knurls 32b, 32b.

In FIG. 6, the transmission unit of the ultrasonic transmitter-receiver system 33 is disposed at a given pitch on the peripheral surface of one of the knurls 32b, 32b, while the reception unit of the same system 33 is disposed at a given pitch on the periphery of the other knurl 32b. In this arrangement, the transmitted wave is determined.

In FIG. 7, the transmission and reception units of the ultrasonic transmitter-receiver system 33 are disposed at a given pitch on one of the knurls 32b, 32b, while a reflector plate is affixed to the periphery of the other knurl 32b. In this arrangement, it is the reflected wave that is determined.

As described before, the ultrasonic transmitter-receiver system 33 is adapted to transmit an ultrasonic wave to the package 1 whose body thickness is kept constant and receive either the transmitted wave or the reflected wave.

The above-mentioned guide means 4 comprises a gripper means 41, a guide means 42 for feeding the gripper 41, and accessory components.

The gripper means 41 may for example be a clip, clip roller, chuck, nip roller or the like, while the guide means 42 may be a suitable combination of such means as a chain, a roller chain, a gear, a guide rail, a sprocket, a screw and so on. The guide means 4 is designed not only to feed the package 1, emerging from the shaking means 2 to the ultrasonic means 3 but to further feed the package downstream. At the stage where the package 1 has been shifted downstream of the ultrasonic means 3, the package 1 evaluated acceptable on the basis of information from the ultrasonic means 3 and the package 1 found unacceptable are discharged at independent positions.

In FIG. 3, the package 1 rated acceptable is chuted down on a first conveyer belt 5, while the package 1 rated unacceptable is chuted on a second conveyer belt 6.

In the inspection of a package 1 containing a flowable material using the above-described apparatus of this invention, the package 1 is first fed to the starting end of the feed belt 21 of the shaking means 2. With its body gripped by the feed belt 21, the package 1 is transported toward the terminal end of the belt 21. During this travel, the package 1 is shaken by the shaking unit 22. By this shaking procedure, the contents of the package 1 are homogenized and the head space (plenum) of the package 1 is evenly dispersed into the contents. Generally, the shaking time is 1 to 40 seconds, the shaking stroke is 1 to 40 mm, and the shaking cycle is 1 to 15 times/second.

After shaking, the package 1 is gripped by the gripper means 41 of the guide means 4 at the terminal end of the feed belt 21 and carried by the guide means 42 in the downstream direction. Meanwhile, the package 1 is not shaken so that the head space dispersed into the contents is shifted or gets together on account of its buoyant force depending on the viscosity of the contents. Generally, the time from completion of shaking to ultrasonic determination is set at 5 to 60 seconds.

The package 1, gripped by the gripper means 41 of the guide means 4, is further guided into the water tank or trough 31 of the ultrasonic means 3. In the water tank or trough 31, with the body thickness of package 1 being kept constant by the body thickness limiter 32, the ultrasonic wave is directed to the package 1, whereby output values such as (a) the difference in sonic velocity between a transmitted wave and a received wave or the sonic velocity of the received wave, (b) the time from transmission to reception, and (c) the degree of attenuation of ultrasonic energy, can be generated and displayed. Since the body thickness of the package 1 is kept constant and there is a body of water around the ultrasonic detection system, a high determination accuracy is assured in accordance with this invention.

The packages 1 subjected in succession to ultrasonic determination are further transferred downstream, where the package 1 rated acceptable on the basis of ultrasonic determination outputs and the package 1 rated unacceptable are discharged in distinct positions for sorting.

EXAMPLES

The following examples are further illustrative of the present invention.

Example 1 (Measurement of reflected waves)

Packaging pouches made of a laminated film having a 12 $\mu$m thick polyester film (outermost layer)/9 $\mu$m thick aluminum foil/15 $\mu$m biaxially oriented nylon film/70 $\mu$m polyethylene film (innermost layer) four-layer structure were filled each with 200 g of liquid food (potage). The maximum package thickness after filling was 30 mm.

The filling (contents) in these packages had a specific gravity of 1.06, a viscosity of 50 cps and a pH value of 6.7, as measured directly after filling (hereinafter referred to as "undegraded product").

The packages after filling were allowed to stand under the conditions specified below to give degraded products varying in degree of degradation:
Early degraded product: Standing at ordinary temperature for 2-3 days after filling
Intermediate degraded product: Standing at ordinary temperature for 5-8 days after filling
Late degraded product: Standing at ordinary temperature for 10-15 days
After standing at a temperature of 40° C. for 2 weeks, the package contents showed a specific gravity of 1.06, a viscosity of 1,500 cps and a pH value of 5.4 and were yoghurt-like (hereinafter referred to as "terminal degraded product").

The packages prepared as above were maintained in a horizontal position and shaken thoroughly. Thereafter, they were allowed to stand in a vertical position for 20 seconds and then introduced into water in a water tank. An ultrasonic transmitter-receiver was brought into contact with one side of each package and a metal-made supporter-reflector with the other side of the package, a distance of 25 mm being maintained between the transmitter-receiver and the reflector.

An ultrasonic wave having a frequency of 1 MHz or 5 MHz was transmitted from the ultrasonic transmitter-receiver and the reflected wave was received with the transmitter-receiver, and the sonic velocity, the time from transmission to reception and the degree of attenuation of the ultrasonic energy were measured.

The results were as shown below. Each test run was performed with 10 packages.

| Reception sonic velocity | | |
|---|---|---|
| 1 MHz | Undegraded product | 1670 ± 2 m/sec |
| | Early degraded product | 1674 ± 2 m sec |
| | Intermediate degraded product | 1677 ± 2 m/sec |
| | Late degraded product | 1680 ± 2 m/sec |
| (Transmission sonic velocity was 1683 ± 2 m/sec.) | | |
| 5 MHz | Undegraded product | 1671 ± 2 m/sec |
| | Early degraded product | 1672 ± 2 m sec |
| | Intermediate degraded product | 1676 ± 2 m/sec |
| | Late degraded product | 1678 ± 2 m/sec |
| (Transmission sonic velocity was 1683 ± 2 m/sec.) | | |
| Time from transmission to reception | | |
| 1 MHz | Undegraded product | 39.46 ± 0.02 $\mu$sec |
| | Early degraded product | 39.50 ± 0.02 $\mu$sec |
| | Intermediate degraded product | 39.57 ± 0.02 $\mu$sec |
| | Late degraded product | 39.60 ± 0.02 $\mu$sec |
| 5 MHz | Undegraded product | 39.50 ± 0.02 $\mu$sec |
| | Early degraded product | 39.53 ± 0.02 $\mu$sec |
| | Intermediate degraded product | 39.58 ± 0.02 $\mu$sec |
| | Late degraded product | 39.64 ± 0.02 $\mu$sec |
| Degree of attenuation | | |
| 1 MHz | Undegraded product | −24.4 ± 0.3 dB |
| | Early degraded product | −20.3 ± 0.3 dB |
| | Intermediate degraded product | −7.5 ± 0.3 dB |
| | Late degraded product | −4.3 ± 0.3 dB |
| | Terminal degraded product | −3.5 ± 0.3 dB |
| 5 MHz | Undegraded product | −25.4 ± 0.3 dB |
| | Early degraded product | −19.5 ± 0.3 dB |
| | Intermediate degraded product | −7.8 ± 0.3 dB |
| | Late degraded product | −4.0 ± 0.3 dB |
| | Terminal degraded product | −2.0 ± 0.3 dB |

Based on the above results, it can be concluded that when the reflected sonic wave velocity, the time from transmission to reception or the degree of ultrasonic energy attenuation is known, the degree of degradation of the package contents can be estimated and that, in the above-mentioned potage case, measurement of the degree of attenuation of reflected waves is particularly effective.

Example 2 (Measurement of transmitted waves)

Packages prepared in the same manner as in Example 1 were maintained in a horizontal position and shaken thoroughly. Then, they were allowed to stand in a vertical position for 20 seconds and thereafter introduced into water in a water tank. An ultrasonic transmitter was disposed on one side of each package and an ultrasonic receiver on the other side, with a distance of 25 mm being maintained between the transmitter and the receiver.

An ultrasonic wave having a frequency of 1 MHz, 2 MHz or 5 MHz was transmitted from the ultrasonic transmitter and the transmitted wave was received with the receiver, and the sonic velocity, the time from transmission to reception and the degree of ultrasonic energy attenuation were measured.

The results were as shown below. Ten packages were used in each test run.

| Reception sonic velocity | | |
|---|---|---|
| 1 MHz | Undegraded product | 1673 ± 2 m/sec |
| | Early degraded product | 1676 ± 2 m sec |
| | Intermediate degraded product | 1680 ± 2 m/sec |
| | Late degraded product | 1683 ± 2 m/sec |
| (Transmission sonic velocity was 1683 ± 2 m/sec.) | | |
| 2 MHz | Undegraded product | 1675 ± 2 m/sec |
| | Early degraded product | 1680 ± 2 m sec |
| | Intermediate degraded product | 1690 ± 2 m/sec |
| | Late degraded product | 1690 ± 2 m/sec |
| (Transmission sonic velocity was 1683 ± 2 m/sec.) | | |
| 5 MHz | Undegraded product | 1676 ± 2 m/sec |

-continued

|  |  |  |
|---|---|---|
|  | Early degraded product | 1677 ± 2 m sec |
|  | Intermediate degraded product | 1683 ± 2 m/sec |
|  | Late degraded product | 1686 ± 2 m/sec |
| (Transmission sonic velocity was 1683 ± 2 m/sec.) | | |
|  | Degree of attenuation | |
| 1 MHz | Undegraded product | −26.5 ± 0.2 dB |
|  | Early degraded product | −24.8 ± 0.2 dB |
|  | Intermediate degraded product | −10.0 ± 0.2 dB |
|  | Late degraded product | −9.5 ± 0.2 dB |
|  | Terminal degraded product | −8.2 ± 0.2 dB |
| 5 MHz | Undegraded product | −26.5 ± 0.2 dB |
|  | Early degraded product | −23.6 ± 0.2 dB |
|  | Intermediate degraded product | −9.8 ± 0.2 dB |
|  | Late degraded product | −8.7 ± 0.2 dB |
|  | Terminal degraded product | −8.1 ± 0.2 dB |

Example 3 (Measurement of transmitted waves)

Packaging pouches made of a laminated film having a 12 μm thick polyester film (outermost layer)/9 μm thick aluminum foil/80 μm thick unstretched polypropylene film (innermost layer) three-layer structure were each filled with 200 g of fluid food (white sauce), the maximum thickness after filling being 30 mm.

The white sauce was used directly after preparation (undegraded product) or after allowing to stand at ordinary temperature for 1 week (intermediate degraded product).

The packages prepared in the above manner were maintained in a horizontal position, shaken well and then allowed to stand in a vertical position for 20 seconds. Thereafter, they were introduced into water in a water tank. An ultrasonic transmitter was disposed on one side of each package and an ultrasonic receiver on the other side, with a distance of 25 mm being maintained between the transmitter and the receiver.

An ultrasonic wave having a frequency of 0.5 MHz or 3 MHz was transmitted from the ultrasonic transmitter and the transmitted wave was received with the receiver and the reception sonic velocity was measured.

The results were as shown below. Ten packages were used in each test run.

|  |  |  |
|---|---|---|
| Reception sonic velocity | | |
| 0.5 MHz | Undegraded product | 1565 ± 2 m/sec |
|  | Intermediate degraded product | 1575 ± 2 m/sec |
| (Transmission sonic velocity was 1683 ± 2 m/sec.) | | |
| 3 MHz | Undegraded product | 1568 ± 2 m/sec |
|  | Intermediate degraded product | 1577 ± 2 m/sec |
| (Transmission sonic velocity was 1683 ± 2 m/sec.) | | |

What is claimed is:

1. An ultrasonic method of inspecting contents of a package comprising:
   shaking said package so as to disperse head space into contents of said package;
   immersing the package in water after shaking;
   disposing an ultrasonic transmitter-receiver system on at least one side of said package and applying pressure to the package to squeeze it to a certain depth, while keeping the body thickness of the package constant;
   transmitting an ultrasonic wave selected from a wavelength region of approximately 0.5 MHz to approximately 20 MHz;
   receiving the ultrasonic wave to obtain output data; and
   evaluating an occurrence or degree of degradation of the contents based upon said output data.

2. An ultrasonic method according to claim 1 wherein said ultrasonic transmitter-receiver system comprises disposing an ultrasonic transmitter on one side of said package and an ultrasonic receiver on the other side, transmitting an ultrasonic wave from said transmitter through the package with said receiver.

3. An ultrasonic method according to claim 1, wherein said ultrasonic transmitter-receiver system disposed on one side of the package is disposed so as to transmit an ultrasonic wave and to receive a reflected wave.

4. An ultrasonic method according to claim 1, wherein said output data comprises at least one of a sonic velocity difference between a transmitted wave and a received wave, the sonic velocity of the received wave, a time interval from transmission of the transmitted wave to reception of the received wave, and a degree of attenuation of an ultrasonic wave.

5. An ultrasonic method according to claim 1, wherein said package is a bag.

6. An ultrasonic method according to claim 1, wherein said contents is fluid food.

* * * * *